United States Patent
Studer et al.

(10) Patent No.: US 11,754,551 B2
(45) Date of Patent: Sep. 12, 2023

(54) REPROGRAMMING CELL AGING

(71) Applicant: MEMORIAL SLOAN-KETTERING CANCER CENTER, New York, NY (US)

(72) Inventors: Lorenz Studer, New York, NY (US); Daniela Cornacchia, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 741 days.

(21) Appl. No.: 16/536,786

(22) Filed: Aug. 9, 2019

(65) Prior Publication Data

US 2020/0003761 A1 Jan. 2, 2020

Related U.S. Application Data

(63) Continuation of application No. PCT/US2018/017843, filed on Feb. 12, 2018.

(60) Provisional application No. 62/457,705, filed on Feb. 10, 2017.

(51) Int. Cl.
*C12N 5/074* (2010.01)
*G01N 33/50* (2006.01)
*C12N 15/90* (2006.01)

(52) U.S. Cl.
CPC ....... *G01N 33/5073* (2013.01); *C12N 5/0607* (2013.01); *C12N 15/907* (2013.01); *G01N 33/5041* (2013.01); *C12N 2310/20* (2017.05)

(58) Field of Classification Search
None
See application file for complete search history.

(56) References Cited

U.S. PATENT DOCUMENTS 5,399,346 A 3/1995 Anderson et al.

FOREIGN PATENT DOCUMENTS

| WO | WO 2008/032905 A1 | 3/2008 |
|----|-------------------|--------|
| WO | WO 2012/076650 A1 | 6/2012 |
| WO | WO 2016/103233 A2 | 6/2016 |
| WO | WO 2016/115407 A1 | 7/2016 |
| WO | WO 2016/210271 A1 | 12/2016 |

OTHER PUBLICATIONS

Takahashi and Yamanaka, Induction of Pluripotent Stem Cells from Mouse Embryonic and Adult Fibroblast Cultures by Defined Factors. Cell (2006) 126, 663-676 (Year: 2006).*
Chen et al., Wip1 deficiency impairs haematopoietic stem cell function via p53 and mTORC1 pathways. Nature Communications (2015), 6:6808, DOI: 10.1038/ncomms7808, pp. 1-11 (Year: 2015).*
TERT telomerase reverse transcriptase [*Homo sapiens* (human)], Gene ID: 7015, archived page from Jan. 2, 2016, https://web.archive.org/web/20160102123455/https://www.ncbi.nlm.nih.gov/gene/7015, [retrieved Aug. 19, 2022] (Year: 2016).*
Liu et al., Editing DNA Methylation in the Mammalian Genome. Cell (2016), 167: 233-247 (Year: 2016).*
Studer et al., Programming and Reprogramming Cellular Age in the Era of Induced Pluripotency. Cell Stem Cell (2015), 16: 591-600 (Year: 2015).*
Sangel et al., The role of Importin-βs in the maintenance and lineage commitment of mouse embryonic stem cells. FEBS Open Bio (2014), 4: 112-120 (Year: 2014).*
Perez-Pinera et al., RNA-guided gene activation by CRISPR-Cas9-based transcription factors. Nature Methods (2013), 10(10): 973-976 (Year: 2013).*
Grafodatskaya et al.,EBV transformation and cell culturing destabilizes DNA methylation in human lymphoblastoid cell lines. Genomics (2010), 95(2): 73-83 (Year: 2010).*
Nicholls et al., Molecular regulation of telomerase activity in aging. Protein Cell (2011), 2(9): 726-738 (Year: 2011).*
Zhang et al., A Transmembrane Accessory Subunit that Modulates Kainate-Type Glutamate Receptors. Neuron (2009), 61: 385-396 (Year: 2009).*
Jung et al., Pharmacological Unmasking Microarray Approach-Based Discovery of Novel DNA Methylation Markers for Hepatocellular Carcinoma. J Korean Med Sci (2012), 2: 594-604 (Year: 2012).*
Komor et al., CRISPR-Based Technologies for the Manipulation of Eukaryotic Genomes. Cell (2017), 168: 20-36 (Year: 2017).*
Anderson, "Prospects for Human Gene Therapy," Science 226:401-409 (1984).
Benayoun et al., "Epigenetic regulation of ageing: linking environmental inputs to genomic stability," Nature Reviews Molecular Cell Biology 16(10):593-610 (2015).
Bicakci et al., "Investigation of the effects of aging on the expression of aquaporin 1 and aquaporin 4 protein in heart tissue," Anatol J Cardiol 17:18-23 (2017).
Blomer et al., "Highly Efficient and Sustained Gene Transfer in Adult Neurons with a Lentivirus Vector," Journal of Virology 71:6641-6649 (1997).
Bregni, et al., "Human Peripheral Blood Hematopoietic Progenitors Are Optimal Targets of Retroviral-Mediated Gene Transfer," Blood 80(6):1418-1422 (1992).
Brigham et al., "Rapid Communication: In vivo Transfection of Murine Lungs with a Functioning Prokaryotic Gene Using a Liposome Vehicle," Am. J. Med. Sci. 298(4):278-281 (1989).
Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy 8:423-430 (1997).

(Continued)

*Primary Examiner* — Samuel C Woolwine
*Assistant Examiner* — Catherine Konopka
(74) *Attorney, Agent, or Firm* — Baker Botts L.L.P.

(57) ABSTRACT

Disclosed herein are methods and compositions for identifying transcriptional and epigenetic age-related markers. Disclosed herein are also methods and compositions for reprogramming cell age by modulating transcriptional and epigenetic age-related markers identified herein. The identified transcriptional and epigenetic age-related markers can also be used for measuring cellular age in a cell or tissue.

9 Claims, 10 Drawing Sheets

(56) References Cited

OTHER PUBLICATIONS

Figures 1A, 1B:
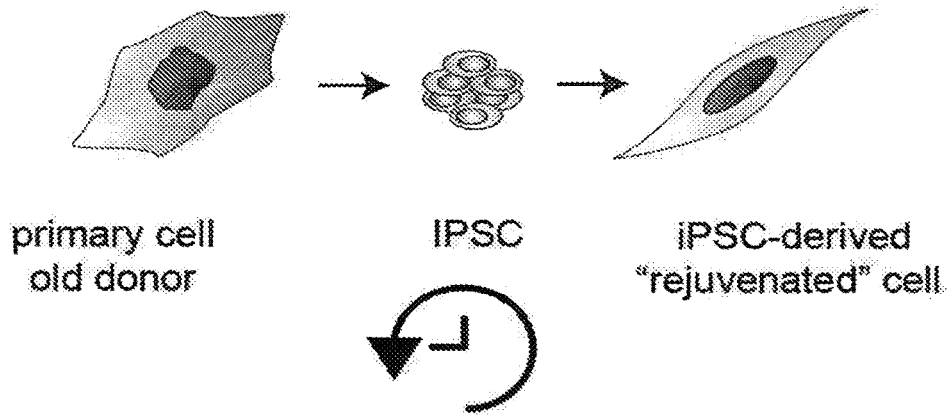

Chiappinelli et al., "Inhibiting DNA Methylation Causes an Interferon Response in Cancer via dsRNA Including Endogenous Retroviruses," Cell 162:974-986 (2015).
Cornacchia et al., "Back and forth in time: Directing age in iPSC-derived lineages," Brain Research (2015) 15 pages.
Cornetta et al., "Gene Transfer into Primates and Prospects for Gene Therapy in Humans," Nucleic Acid Research and Molecular Biology 36:311-322 (1987).
Danos et al., "Safe and efficient generation of recombinant retroviruses with amphotropic and ecotropic host ranges," Proc. Natl. Acad. Sci. USA 85:6460-6464 (1988).
Dominguez et al., "Beyond editing: repurposing CRISPR-Cas9 for precision genome regulation and interrogation," Nature Reviews Molecular Cell Biology 17(1):5-15 (2016).
Eglitis et al., "Retroviral Vectors for Introduction of Genes into Mammalian Cells," Bio-Techniques 6(7):608-614 (1988).
Felgner et al., "Lipofection: A highly efficient, lipid-mediated DNA-transfection procedure," Proc. Natl. Acad. Sci. U.S.A. 84:7413-7417 (1987).
Feser et al., "Chromatin structure as a mediator of aging," FEBS Letters 585:2041-2048 (2011).
Fraga et al., "Epigenetics and aging: the targets and the marks," TRENDS in Genetics 23(8):413-418 (2007).
Friedmann, "Progress toward Human Gene Therapy," Science 244:1275-1281 (1989).
Fuchs et al., "Human endogenous retrovirus K (HML-2) RNA and protein expression is a marker for human embryonic and induced pluripotent stem cells," Retrovirology 10:115 (2013) 6 pages.
Ganat et al., "Identification of embryonic stem cell-derived midbrain dopaminergic neurons for engraftment," J Clin Invest 122(8):2928-2939 (2012).
Glass et al., "Gene expression changes with age in skin, adipose tissue, blood and brain," Genome Biology 14:R75 (2013).
Grow et al., "Intrinsic retroviral reactivation in human preimplantation embryos and pluripotent cells," Nature 522(7555):221-225 (2015).
Hilton et al., "Epigenome editing by a CRISPR/Cas9-based acetyltransferase activates genes from promoters and enhancers," Nature Biotechnology 33(5):510-517 (2015).
Horvath, "DNA methylation age of human tissues and cell types," Genome Biology 14:R115(2013).
Hughes et al., "Retroviral Gene Transfer to Primitive Normal and Leukemic Hematopoiet-ic Cells Using Clinically Applicable Procedures," J. Clin. Invest. 89:1817-1824 (1992).
International Search Report dated Jun. 18, 2018 in International Application No. PCT/US18/17843.
Johnson et al., "The Role of DNA Methylation in Aging, Rejuvenation, and Age-Related Disease," Rejuvenation Research 15(5):483-494 (2012).
Johnson, "Gene Therapy for Cystic Fibrosis," Chest 107:77S-83S (1995).
Kearns et al., "Functional annotation of native enhancers with a Cas9-histone demethylase fusion," Nature Methods 12(5):401-403 (2015).
Kido et al., "Use of a retroviral vector with an internal opsin promoter to direct gene expression to retinal photoreceptor cells," Current Eye Research 15:833-844 (1996).
Lapasset et al., "Rejuvenating senescent and centenarian human cells by reprogramming through the pluripotent state," Genes & Development 25:2248-2253 (2011).
Le Gal La Salle et al., "An Adenovirus Vector for Gene Transfer into Neurons and Glia in the Brain," Science 259:988-990 (1993).
Li et al., "Human Endogenous Retrovirus-K Contributes to Motor Neuron Disease," Science Translational Medicine 7(307):1-13 (2015).
Lister et al., "Global Epigenomic Reconfiguration During Mammalian Brain Development," Science 341(6146):1237905-1237905 (2013).
Liszczak et al., "Genomic Targeting of Epigenetic Probes Using a Chemically Tailored Cas9 System," PNAS 114(4):1-6 (2017).
Liu et al., "Editing DNA Methylation in the Mammalian Genome," Cell, 167(1):233-247 (2016).
Lopez-Otin et al., "The Hallmarks of Aging," Cell 153:1194-1217 (2013).
Mahmoudi et al., "Aging and reprogramming: a two-way street," Current Opinion in Cell Biology 24:744-756 (2012).
Marion et al., "Telomeres Acquire Embryonic Stem Cell Characteristics in Induced Pluripotent Stem Cells," Cell Stem Cell 4:141-154 (2009).
Mertens et al., "Directly Reprogrammed Human Neurons Retain Aging-Associated Transcriptomic Signatures and Reveal Age-Related Nucleocytoplasmic Defects," Cell Stem Cell 17:705-718 (2015).
Miller et al., "Generation of Helper-Free Amphotropic Retroviruses That Transduce a Dominant-Acting, Methotrexate-Resistant Dihydrofolate Reductase Gene," Mol. Cell. Biol. 5(3):431-437 (1985).
Miller et al., "Human iPSC-Based Modeling of Late-Onset Disease via Progerin-Induced Aging," Cell Stem Cell 13:691-705 (2013).
Miller et al., "Improved Retroviral Vectors for Gene Transfer and Expression," Biotechniques 7:980-990 (1989).
Miller et al., "Redesign of Retrovirus Packaging Cell Lines to Avoid Recombination Leading to Helper Virus Production," Mol. Cell. Biol. 6(8):2895-2902 (1986).
Miller, "Retrovirus Packaging Cells," Human Gene Therapy 1:5-14 (1990).
Miyoshi et al., "Stable and efficient gene transfer into the retina using an HIV-based lentiviral vector," Proc. Natl. Acad. Sci. U.S.A. 94:10319-10323 (1997).
Moen, "Directions in Gene Therapy," Blood Cells 17:407-416 (1991).
Naldini et al., "In Vivo Gene Delivery and Stable Transduction of Nondividing Cells by a Lentiviral Vector," Science 272:263-267 (1996).
Ong et al., "Novel region discovery method for Infinium 450K DNA methylation data reveals changes associated with aging in muscle and neuronal pathways," Aging Cell 13:142-155 (2014).
Ono et al., "Plasmid DNAs directly injected into mouse brain with lipofectin can be incorporated and expressed by brain cells," Neuroscience Letters 117:259-263 (1990).
Owens et al., "Effective Targeted Gene Knockdown in Mammalian Cells Using the piggyBac Transposase-based Delivery System," Molecular Therapy-Nucleic Acids 2:e137, 5 pages (2013).
Partial Supplementary European Search Report dated Dec. 14, 2020 in Application No. EP 18751577.
Per Holmfeldt et al., "Functional screen identifies regulators of murine hematopoietic stem cell repopulation," The Journal of Experimental Medicine 213(3):433-449 (2016).
Rosenberg et al., "Gene Transfer into Humans—Immunotherapy of Patients with Advanced Melanoma, Using Tumor-Infiltrating Lymphocytes Modified By Retroviral Gene Transduction," N. Engl. J Med 323:570-578 (1990).
Roulois et al., "DNA-Demethylating Agents Target Colorectal Cancer Cells by Inducing Viral Mimicry by Endogenous Transcripts," Cell 162:961-973 (2015).
Sharp, "Gene Therapy," The Lancet 337:1277-1278 (1991).
Steinbeck et al., "Optogenetics enables functional analysis of human embryonic stem cell-derived grafts in a Parkinson's disease model," Nature Biotechnology 33(2):204-209 (2015).
Straubinger et al., "Liposomes as Carriers for Intracellular Delivery of Nucleic Acids," Methods in Enzymology 101:512-527 (1983).
Studer et al., "Programming and Reprogramming Cellular Age in the Era of Induced Pluripotency," Cell Stem Cell 16:591-600 (2015).
Suhr et al., "Mitochondrial Rejuvenation after Induced Pluripotency," PLoS ONE 5(ll):e14095 (2010) 9 pages.
Thakore et al., "Editing the Epigenome: Technologies for Programmable Transcriptional Modulation and Epigenetic Regulation," Nat Methods 13(2):127-137 (2016).
Tolstoshev et al., "Gene expression using retroviral vectors," Current Opinion in Biotechnology 1:55-61 (1990).

(56) References Cited

OTHER PUBLICATIONS

Wang et al., "Artificial Induction of Native Aquaporin-1 Expression in Human Salivary Cells," Journal of Dental Research 96(4):444-449 (2017).
Wolff et al., "Direct Gene Transfer into Mouse Muscle in Vivo," Science 247:1465-1468 (1990).
Wu et al., "Receptor-mediated Gene Delivery and Expression in Vivo," Journal of Biolog-ical Chemistry 263:14621-14624 (1988).
Wu et al., "Targeting Genes: Delivery and Persistent Expression of a Foreign Gene Driven by Mammalian Regulatory Elements in Vivo," Journal of Biological Chemistry 264:16985-16987 (1989).
Xu et al., "Correction of the enzyme deficiency in hemapoietic cells of Gaucher patients using a clinically acceptable retroviral supernatant transduction protocol," Exp. Hemat. 22:223-230 (1994).

* cited by examiner

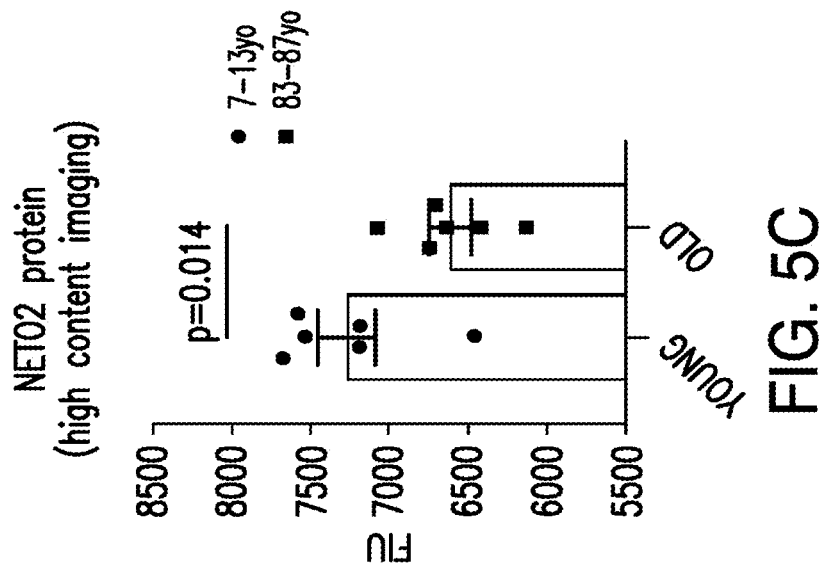
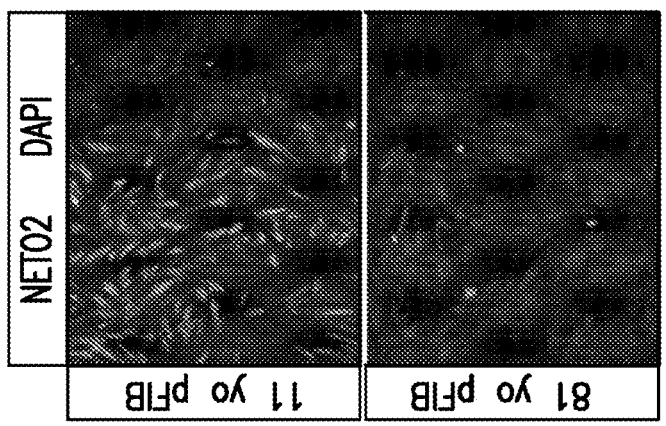
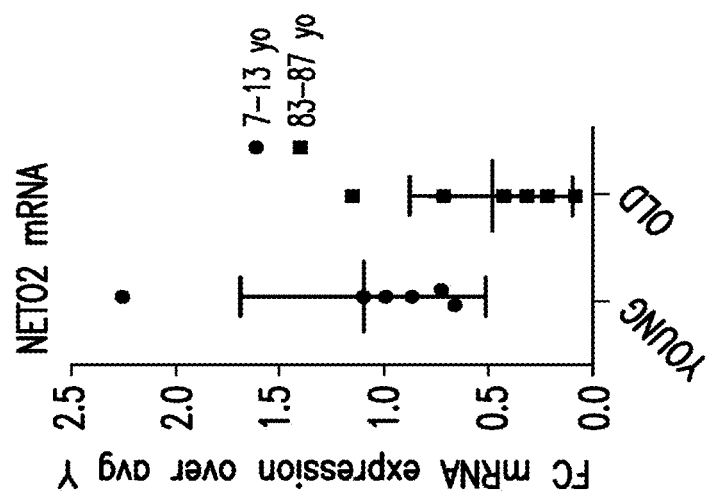
FIG. 5A
FIG. 5B
FIG. 5C

REPROGRAMMING CELL AGING

CROSS-REFERENCE TO RELATED APPLICATION

This application is a Continuation of International Application No. PCT/US2018/017843, filed Feb. 12, 2018, which claims priority to U.S. Provisional Application No.: 62/457,705 filed on Feb. 10, 2017 the contents of each of which are hereby incorporated by reference in their entireties, to each of which priority is claimed.

1. INTRODUCTION

The present invention relates to the identification of transcriptional and epigenetic changes associated with chronological aging and the modulation of a cell, for example a cell in a culture, tissue or subject, to achieve a transcriptional and epigenetic profile characteristic of early (young) chronological age and thereby "rejuvenate" the cell, tissue, or subject; or alternatively, to achieve a transcriptional and epigenetic profile of a late (old) chronological age, and thereby "age" the cell, tissue, or subject.

2. BACKGROUND OF THE SUBJECT MATTER

Inducing pluripotency in somatic cells has broken the dogma of the unidirectionality of cell fate decisions. In the last decade the stem cell field has learned to master the manipulation of cell identity by reversing cell fate specification and directing differentiation towards any desirable lineage. At the same time, a separate aspect of cell identity that is equally reprogrammed by induced pluripotency has received only minor attention, namely, the resetting of cellular age. It has often been observed that cells derived from induced pluripotent stem cells (iPSC) are functionally immature, which is believed to reflect a fetal-like state and indicate that running the differentiation program backwards to pluripotency rewinds the developmental clock to zero[1,2]. However, beyond this loss of developmental age, it has been shown that reprogramming cells from old individuals can also erase a set of cellular hallmarks and signs of functional decay associated with the chronological age of the donor, leaving cells biologically rejuvenated[3-7]. The molecular mechanisms leading to the re-acquisition of cellular youthfulness have not been investigated, yet this phenomenon suggests that several aspects of cellular aging may not be the result of irreparable damage but could potentially be reversed by epigenetic reprogramming. There is therefore a need to determine which aspects of physiological aging are driven by reversible changes to the transcriptome and epigenome, and to understand how inducing pluripotency rewrites this code to unlock the biological information for youth.

3. SUMMARY OF THE INVENTION

The present invention relates to identification of reversible changes to the transcriptome and epigenome associated with chronological age of a subject, and to modulation of those changes to effectively "reset" the apparent, although not the actual, chronological age of the subject. It is based, at least in part, on the discoveries of transcriptomic and epigenomic signatures of aged cells and age-sensitive genomic regions that are transcriptionally and epigenetically reset in iPSC and maintained in a "young" state in re-differentiated cells. These findings provide proof of principle for transcriptomic and epigenomic rejuvenation through reprogramming and also uncover novel potential aging determinants.

In one aspect, the presently disclosed subject matter provides methods for reprograming cell age. In certain embodiments, the method comprises administrating to the cell an epigenetic engineering system, in which the epigenetic engineering system alters an epigenetic characteristic at a target genome sequence of the cell. In certain embodiments, the epigenetic engineering system is a CRISPR/Cas9 system, which comprises a Cas9 molecule and a guided RNA (gRNA). In certain embodiments, the Cas9 molecular is conjugated with an epigenetic enzyme, and the gRNA comprises a targeting domain that is complementary with a target sequence of the target genome sequence.

In certain non-limiting embodiments, the epigenetic characteristic is selected from the group consisting of a DNA methylation, a DNA demethylation, a histone methylation, a histone demethylation, a histone acetylation, a histone deacetylation and combinations thereof. In certain embodiments, the target genome sequence is selected from the group consisting of coding genes, regulatory sequences, and non-coding sequences. In certain non-limiting embodiments, the epigenetic enzyme is selected from the group consisting of histone methyltransferases, histone demethylases, histone acetyltransferases, histone deacetylases, nucleic acid methyltransferases, and nucleic acid demethylases. In certain embodiments, the Cas9 molecule is a d-Cas9 molecule.

In certain non-limiting embodiments, the target genome sequence is selected from the group consisting of NETO2 gene, RANBP17 gene, AQP1 gene, and CADPS gene. In certain embodiments, the epigenetic enzyme is a DNA demethylase, and the target genome sequence is selected from the group consisting of NETO2 gene and RANBP17 gene, in which the expression of NETO2 gene or RANBP17 gene is upregulated. In certain embodiments, the epigenetic enzyme is a DNA demethylase, and the target genome sequence is selected from the group consisting of AQP1 gene and CADPS gene, in which the expression of AQP1 gene or CADPS gene is downregulated. In certain embodiments, the epigenetic enzyme is a DNA demethylase, and the target genome sequence is selected from the group consisting of promoter sequences of NETO2 gene and RANBP17 gene, in which the expression of NETO2 gene or RANBP17 gene is upregulated. In certain embodiments, the target genome sequence is HERV-K.

In another aspect, the presently disclosed subject matter provides methods for reprogramming cell age. In certain embodiments, the method includes administrating to the cell a genetic engineering system, in which the genetic engineering system alters the expression of a target genome sequence of the cell. In certain embodiments, the genetic engineering system is a CRISPR/Cas9 system, which comprises a Cas9 molecule and a guided RNA (gRNA). In certain embodiments, the Cas9 molecular is conjugated to a transcription modulator, and the gRNA comprises a targeting domain that is complementary with a target sequence of the target genome sequence. In certain embodiments, the genetic engineering system comprises a short hairpin RNA (shRNA) that is complementary to a mRNA of the target genome sequence.

In certain non-limiting embodiments, the target genome sequence is selected from the group consisting of NETO2 gene, RANBP17 gene, AQP1 gene, and CADPS gene, and HERV-K gene. In certain embodiments, the genetic engineering system upregulates the expression of NETO2 gene or RANBP17 gene. In certain embodiments, the genetic engineering system downregulates the expression of AQP1 gene, CADPS gene, or HERV-K gene.

In another aspect, the presently disclosed subject matter provides methods for reprogramming cell age. In certain embodiments, the method includes administration to the cell a compound, in which the compound modifies an epigenetic marker of the cell genome-wide. In certain non-limiting embodiments, the epigenetic marker is selected from the group consisting of nucleic acid methylations, nucleic acid demethylation, histone methylations, histone demethylations, histone acetylation, and histone deacetylations. In certain non-limiting embodiments, the epigenetic marker is selected from the group consisting of H3K9me3, H3K27me3, and 5mC DNA methylation.

In another aspect, the presently disclosed subject matter provides methods for selecting a compound for reprogramming cell age. In certain embodiments, the method includes administrating the compound to a primary cell obtained from an old donor; administrating the compound to a re-differentiated induced pluripotent stem cell (iPSC) derived from the primary cells, in which the re-differentiated cell has the same cell type as the primary cell; measuring levels of age-associated transcriptional and epigenetic markers of the primary cell and the re-differentiated cell; and comparing the levels of the age-associated transcriptional or epigenetic markers of the primary cell and the re-differentiated cell. In certain non-limiting embodiments, the transcriptional marker is selected from the group consisting of NETO2 RNA, RANBP17 mRNA, AQP1 mRNA, and CADPS mRNA. In certain non-limiting embodiments, the epigenetic marker is selected from the group consisting of nucleic acid methylations, nucleic acid demethylation, histone methylations, histone demethylations, histone acetylation, and histone deacetylations. In certain non-limiting embodiments, the epigenetic marker is selected from the group consisting of H3K9me3, H3K27me3, and 5mC DNA methylation.

In another aspect, the presently disclosed subject matter provides methods for determining transcriptional and epigenetic markers associated with aging. In certain embodiments, the method includes measuring transcriptional and epigenetic profiles of a primary cell obtained from an old donor; measuring transcriptional and epigenetic profiles of a re-differentiated cell derived from the primary cell; comparing the transcriptional and epigenetic profiles of the primary cell with the transcriptional and epigenetic profiles of the re-differentiated cell; and determining transcriptional and epigenetic markers that are differentially expressed between the primary cell and the differentiated cell.

In another aspect, the presently disclosed subject matter provides methods for determining tissue-specific transcriptional and epigenetic markers associated with aging. In certain embodiments, the method includes measuring transcriptional and epigenetic profiles of a primary tissue obtained from an old donor; measuring transcriptional and epigenetic profiles of a primary tissue obtained from a young donor, in which the primary tissues from the old donor and the young donor have the same tissue origin; comparing the transcriptional and epigenetic profiles of the primary tissue from the old donor with the transcriptional and epigenetic profiles of the primary tissue from the young donor; and determining transcriptional and epigenetic markers that are differentially expressed between the old and young donors. In certain embodiments, the method further including: measuring the transcriptional and epigenetic markers in a re-differentiated iPSC derived from a primary cell obtained from the primary tissue of the old donor, in which the re-differentiated iPSC and the primary cell have the same cell type; comparing the transcriptional and epigenetic markers of the re-differentiated iPSC and the transcriptional and epigenetic markers of the primary tissue from the young donor; and determining whether the markers are differentially expressed between the re-differentiated iPSC from the old donor and the primary tissue from the young donor. In certain embodiments, the tissue origin is a frontal cortex region or a substantia nigra region of brain.

In another aspect, the presently disclosed subject matter provides epigenetic engineering systems. In certain embodiments, the system includes a gRNA molecule including a target domain that is complementary with a target sequence of a target genome sequence of a cell, and a Cas9 molecular conjugated with an epigenetic enzyme. In certain non-limiting embodiments, the epigenetic enzyme is selected from the group consisting of histone methyltransferases, histone demethylases, histone acetyltransferases, histone deacetylases, nucleic acid methyltransferases, and nucleic acid demethylases. In certain embodiments, the Cas9 molecule is d-Cas9. In certain non-limiting embodiments, the target genome sequence is selected from the group consisting of NETO2 gene, RANBP17 gene, AQP1 gene, CADPS gene, promoter sequences of NETO2 gene, promoter sequences of RANBP17 gene, promoter sequences of AQP1 gene, promoter sequences of CADPS gene, HERV-K gene, and promoter sequences of HERV-K gene. In certain non-limiting embodiments, the epigenetic enzyme is a DNA demethylase, and the target genome sequence is selected from the group consisting of promoter sequences of NETO2 gene and promoter sequences of RANBP17 gene.

In another aspect, the presently disclosed subject matter provides genetic engineering systems. In certain embodiments, the system includes a gRNA molecule including a target domain that is complementary with a target sequence of a target genome sequence of a cell, a Cas9 molecular conjugated with a transcription modulator. In certain non-limiting embodiments, the target genome sequence is selected from the group consisting of NETO2 gene, RANBP17 gene, AQP1 gene, CADPS gene, and HERV-K gene

4. BRIEF DESCRIPTION OF THE FIGURES

FIGS. 1A-1B. In vitro paradigm to study cellular aging and their rejuvenation in primary cells, iPSCs and iPSC-derived cells[2] FIG. 1A: Primary cells are reprogrammed into iPSCs and differentiated into the same original cell type. FIG. 1B: Illustration of 6 age-related cellular hallmarks that distinguish cells from aged vs. young donors, and that are rejuvenated in iPSC-derived cells. (Adapted from Studer, L., Vera, E. & Cornacchia, D. Programming and Reprogramming Cellular Age in the Era of Induced Pluripotency. Cell stem cell 16, 591-600 (2015).)

Figure 2A:
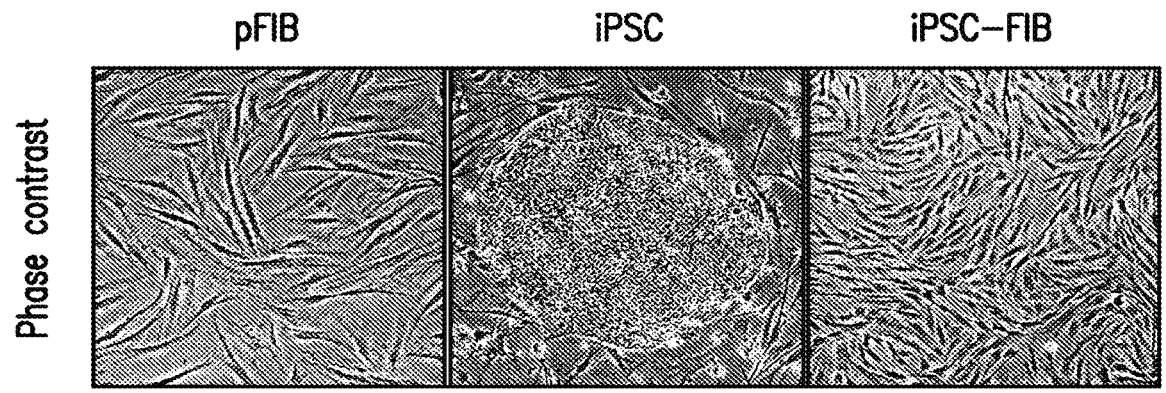
Figure 2B:
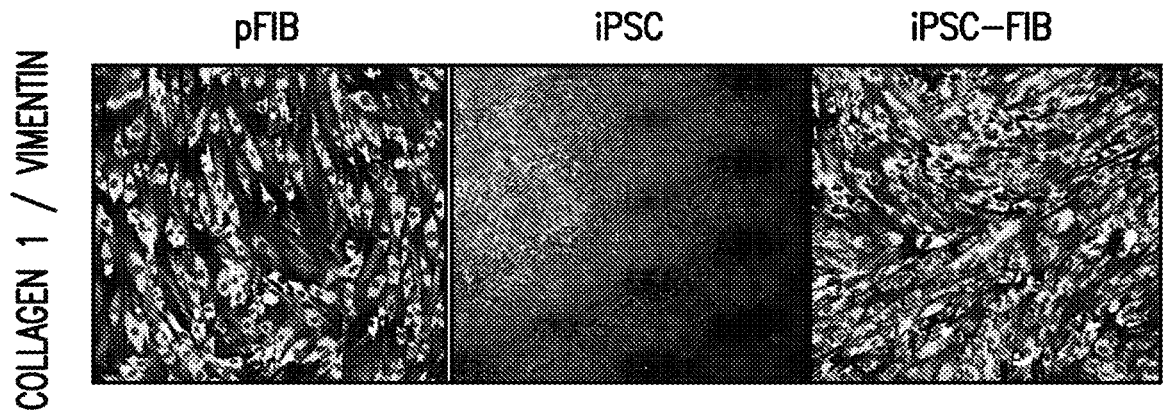
Figure 2C:
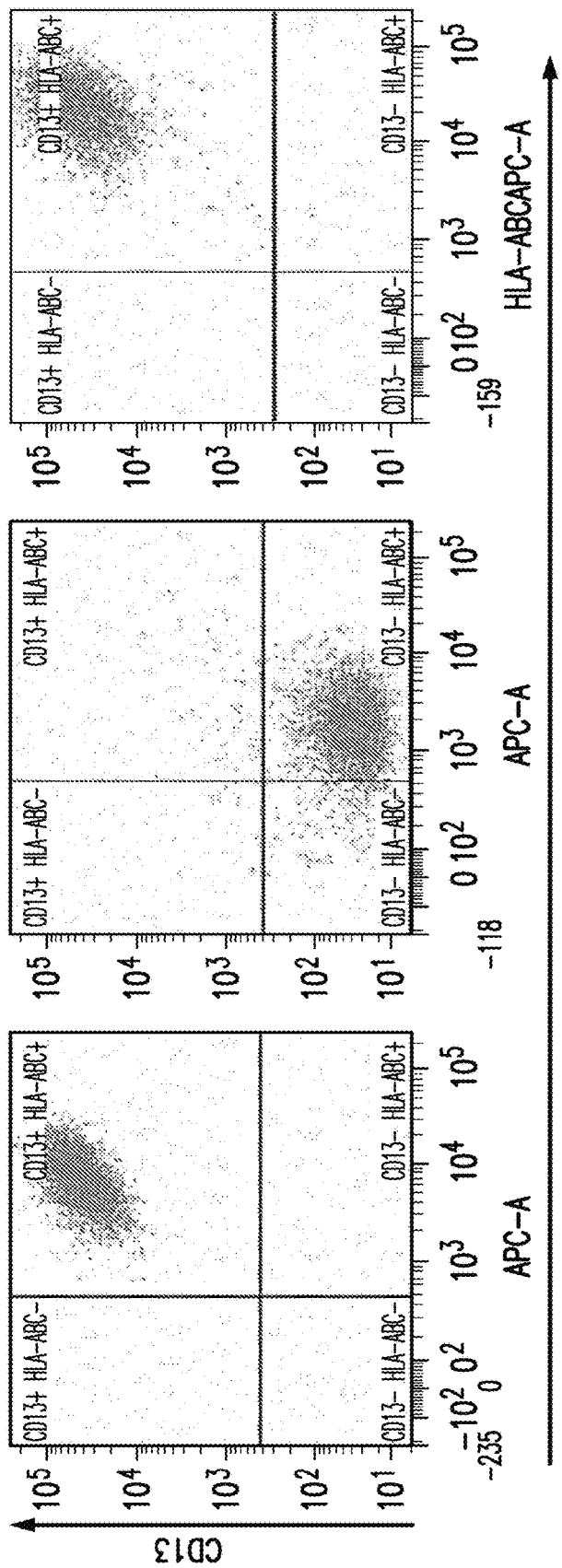
Figure 2D:
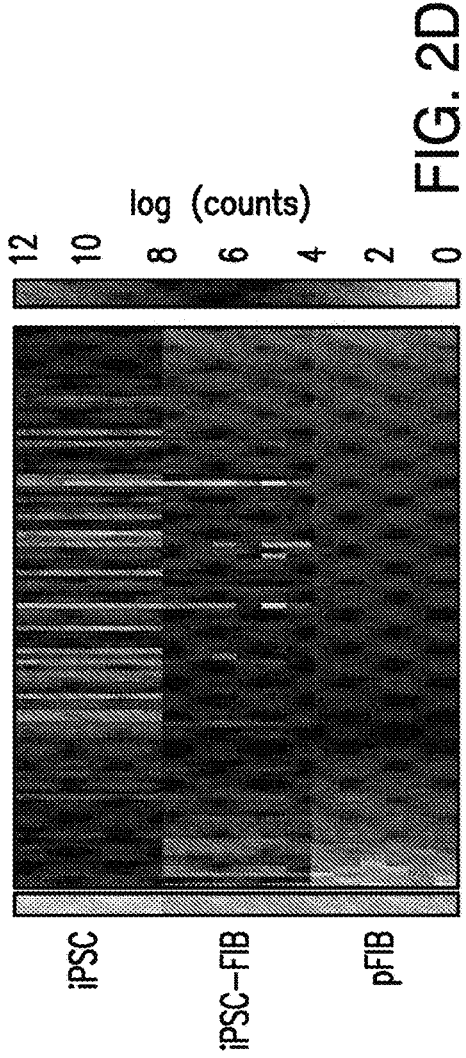

FIGS. 2A-2D. QC measures of iPSC-derived fibroblasts. FIG. 2A: Morphology of primary fibroblasts (pFIB), iPSC and iPSC-derived fibroblasts (iPSC-FIB). FIG. 2B: Fibroblast markers Vimentin and Collagen I expression is reestablished following differentiation to iPSC-fibroblasts. FIG. 2C: FACS analysis by fibroblast markers CD13 and HLA-ABC in iPSC-fibroblasts. FIG. 2D: Gene expression profile of the top differentially expressed genes between primary fibroblasts and iPSC shows that iPSC-fibroblasts closely resemble primary fibroblasts (Pearson corr.=0.91).

Figure 3A:
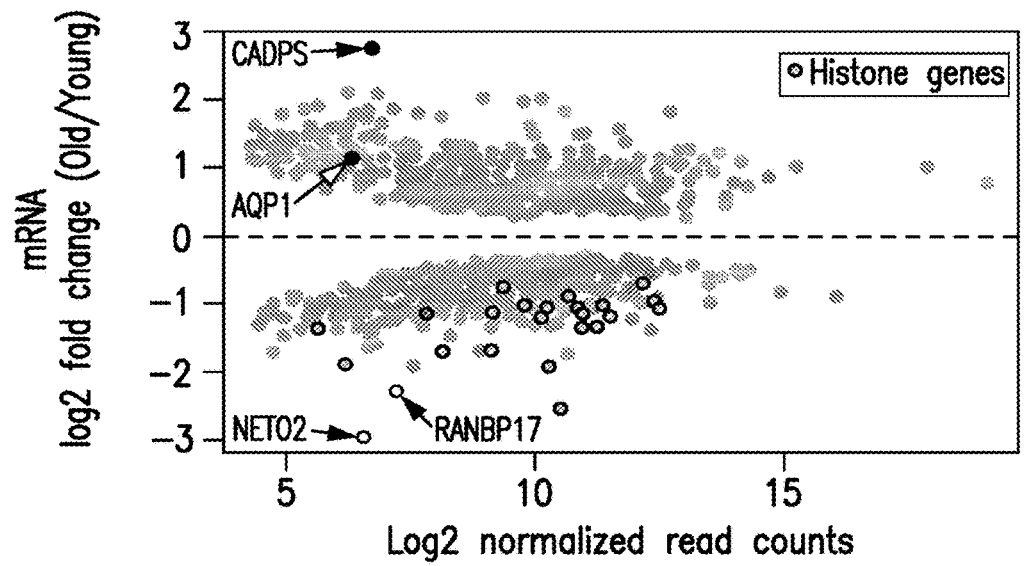
Figure 3B:
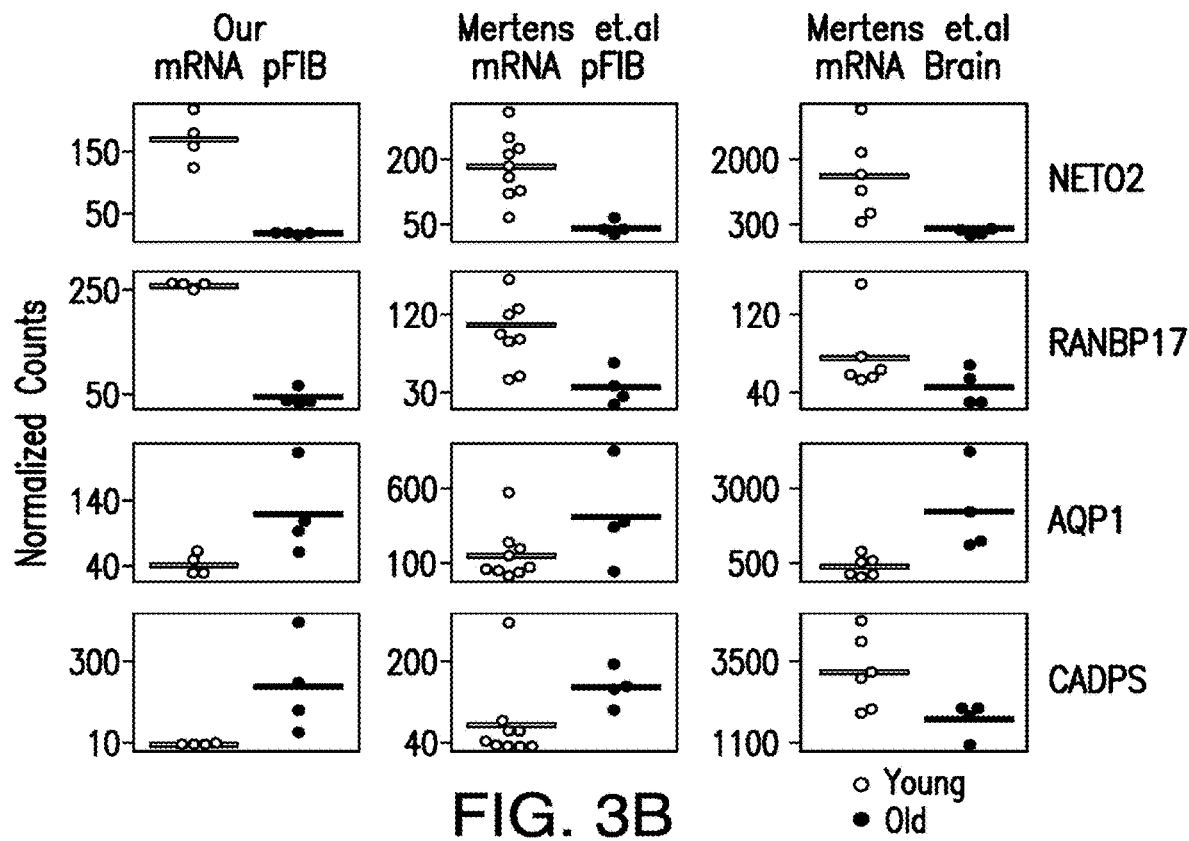
Figure 3C:
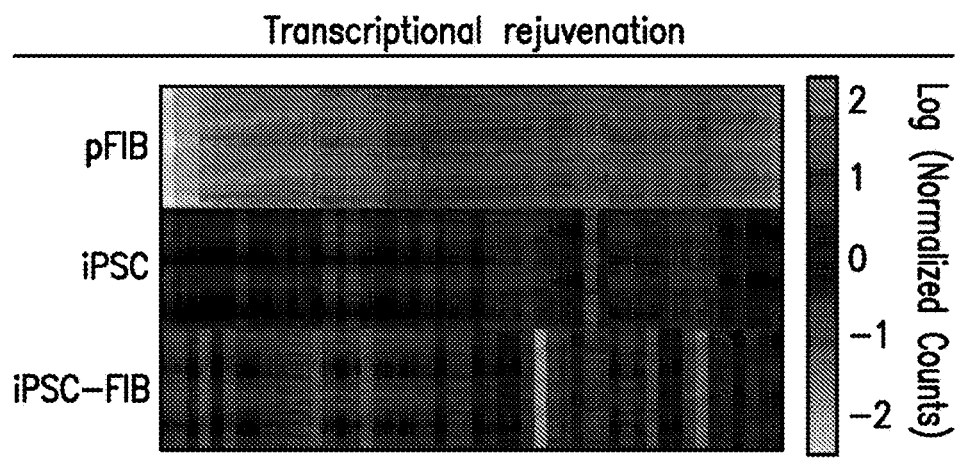
Figure 3D:
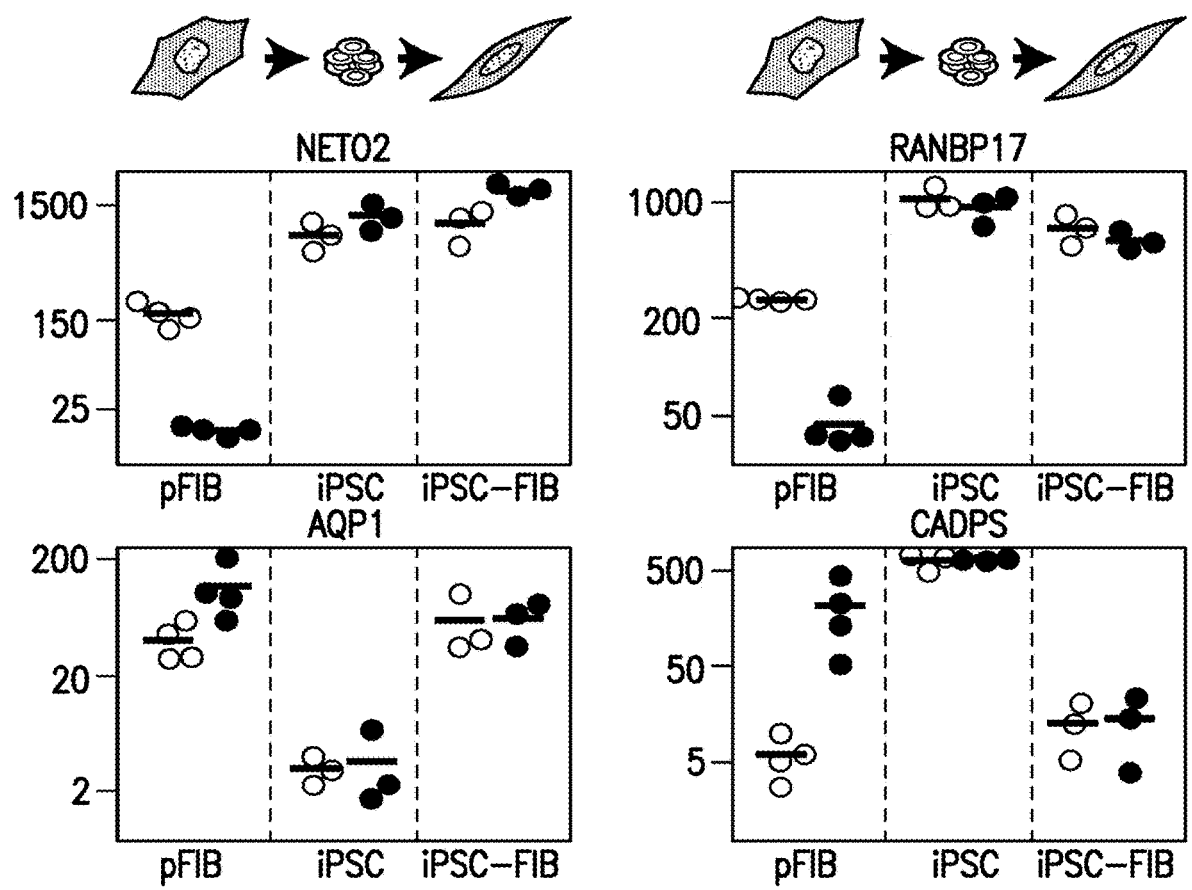
Figure 3E:
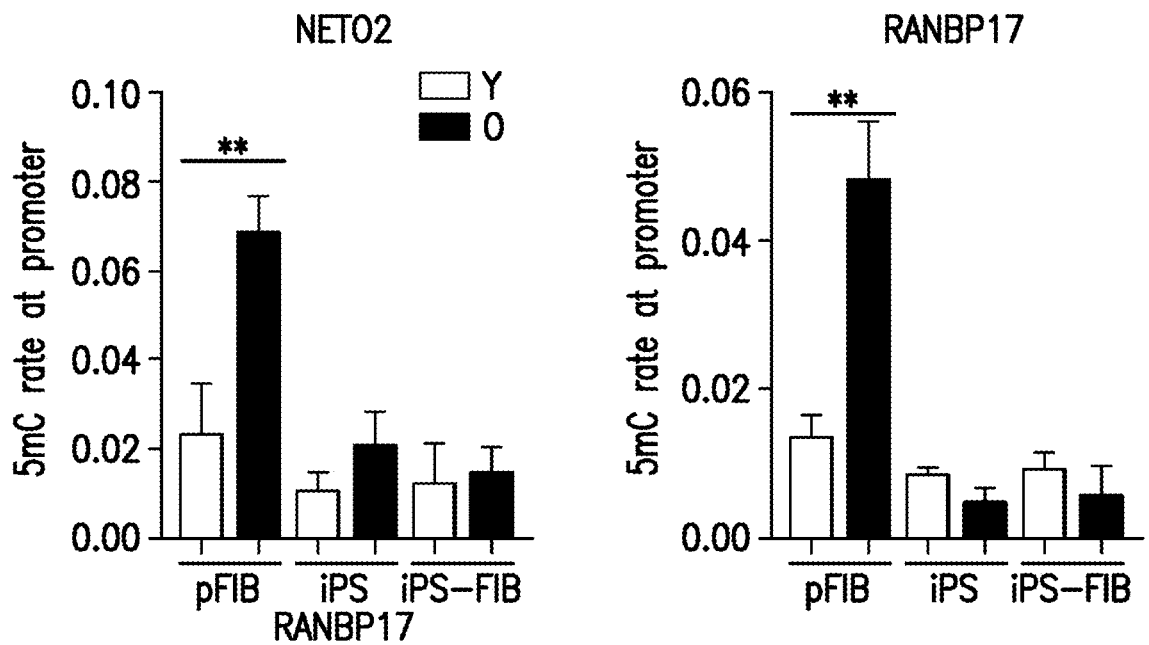
Figure 3F:
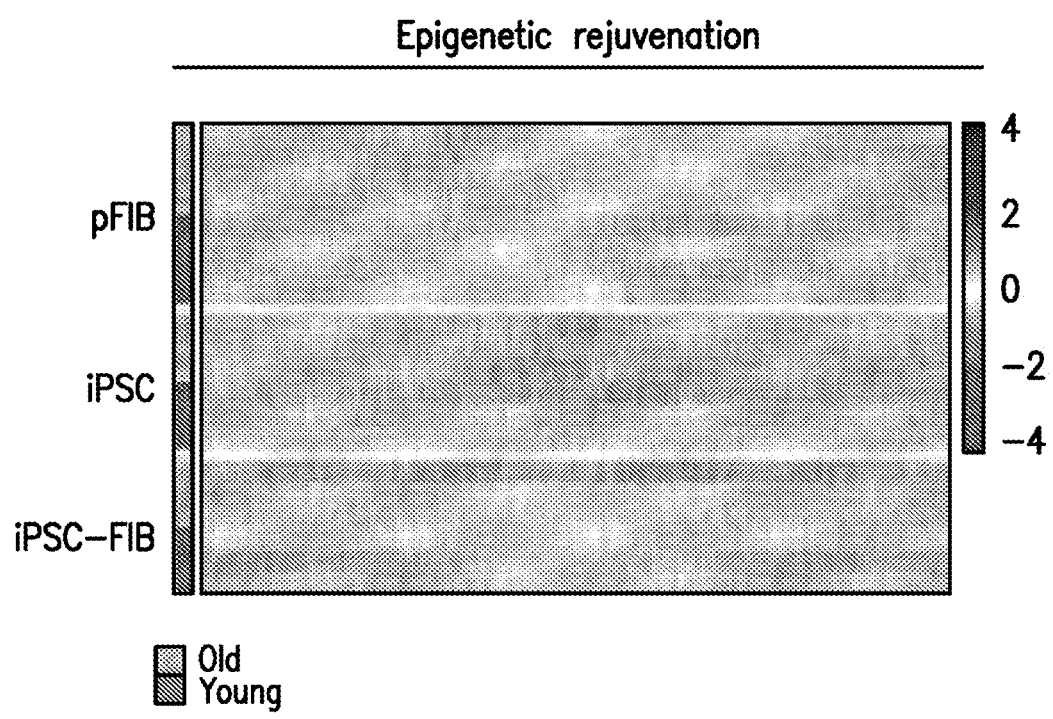

FIGS. 3A-3F. Transcriptional aging signature and its reset upon reprogramming and re-differentiation. FIG. 3A: RNA-seq analysis identified differentially expressed genes in primary fibroblast from young vs. old donors. FIG. 3B: Overlap with a published data set of young vs. old fibroblasts and brain tissues identifies consistent age-dependent genes across datasets[12]. NETO2, RANBP17, AQP1, CADPS were identified as fibroblast aging genes. NETO2, RANBP17, AQP1 were identified as aging genes shared between fibroblasts and brain tissue. FIG. 3C: Transcriptional signature that distinguishes old from young pFIB is not detectable in matched iPSCs and iPSC-FIBs. Values indicate log fold change in expression between young and old donor groups. (3D) Normalized expression of candidate age-related transcripts show differential expression in pFIB but comparable levels in old vs. young-derived iPSCs or iPSC-FIBs. FIG. 3E: "Rejuvenation" of DNA methylation levels at promoter regions of aging genes NETO2 and RANBP17. Decreased expression of NETO2 and RANBP17 in old pFIB correlates with significantly higher methylation (5mC) of promoter regions. 5mC rate is restored to young-like levels in iPSC and iPSC-FIB of both donor groups. FIG. 3F: Epigenetic signature of differential DNA methylation patterns in aged vs young pFIBs are erased after reprogramming in both iPSCs and iPSC-derived FIBs.

Figure 4A:
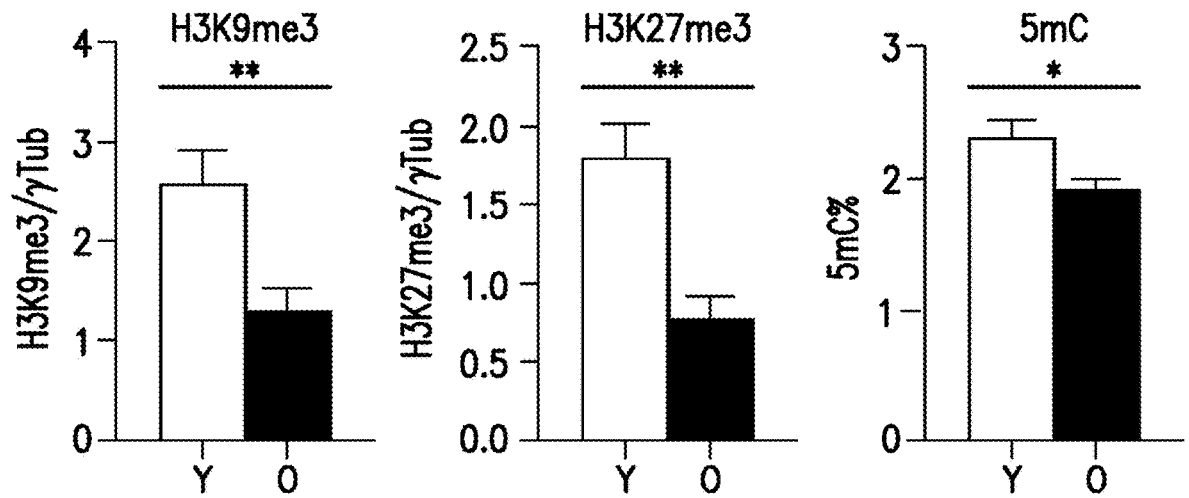
Figure 4B:
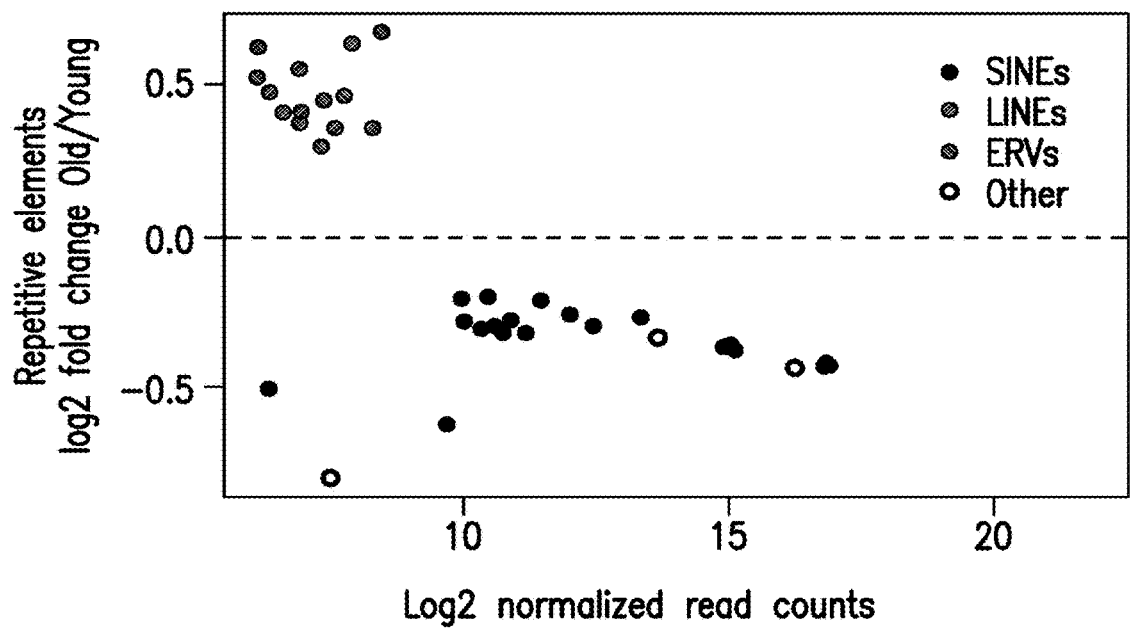

FIGS. 4A-4B. Loss of heterochromatin and deregulated expression of transposable elements in old vs. young fibroblasts. FIG. 4A: Decreased levels of constitutive (H3K9me3) and facultative heterochromatin (H3K27me3) histone modifications and 5mC DNA methylation in old vs. young primary fibroblasts. FIG. 4B: Total RNA Seq analysis shows dramatic deregulation of transposable elements across three main classes (LINE=Long interspersed nuclear elements, SINE=Short interspersed nuclear elements, ERV=endogenous retroviruses).

FIGS. 5A-5C. Validation of NETO2 expression levels as an aging marker. FIG. 5A: RT-qPCR of NETO2 mRNA levels in an independent set of primary fibroblasts obtained from 6 young (7-13y) and 6 old (83-87 y) donors. FIG. 5B: Representative immunofluorescence of NETO2 protein levels in primary fibroblasts obtained from young (11y) and old (81y) donors. FIG. 5C: High content imaging and quantification of NETO2 protein expression in primary fibroblasts obtained from young and old donors.

Figure 6B:
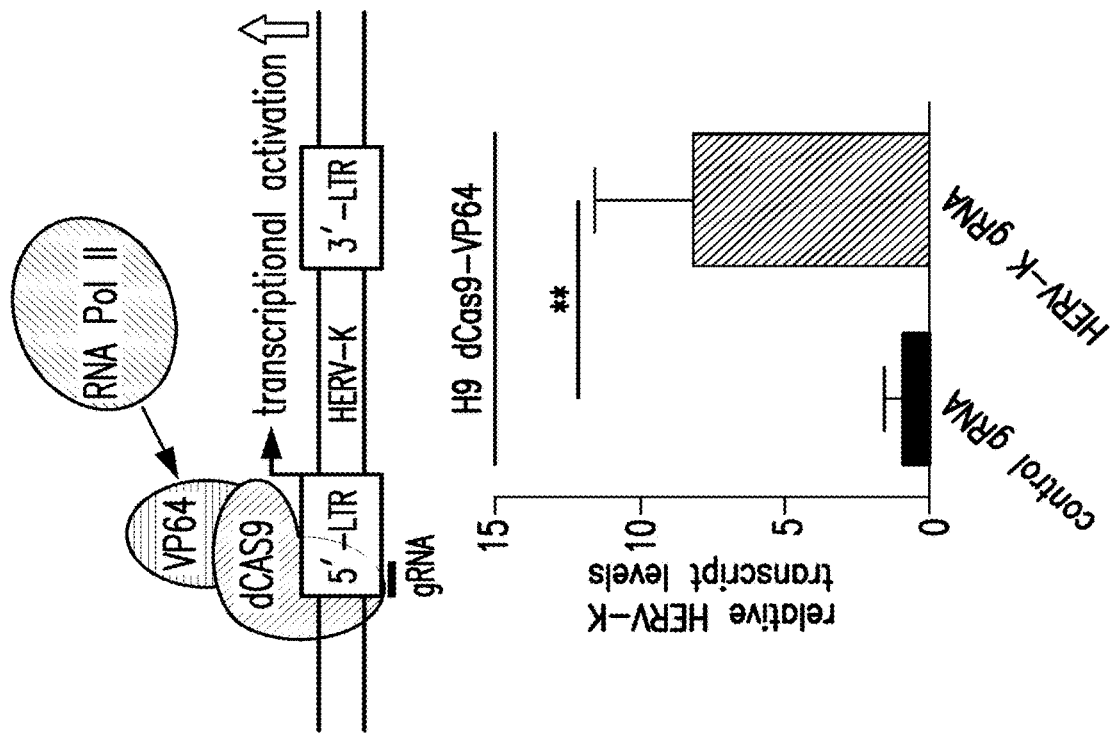
Figure 6A:
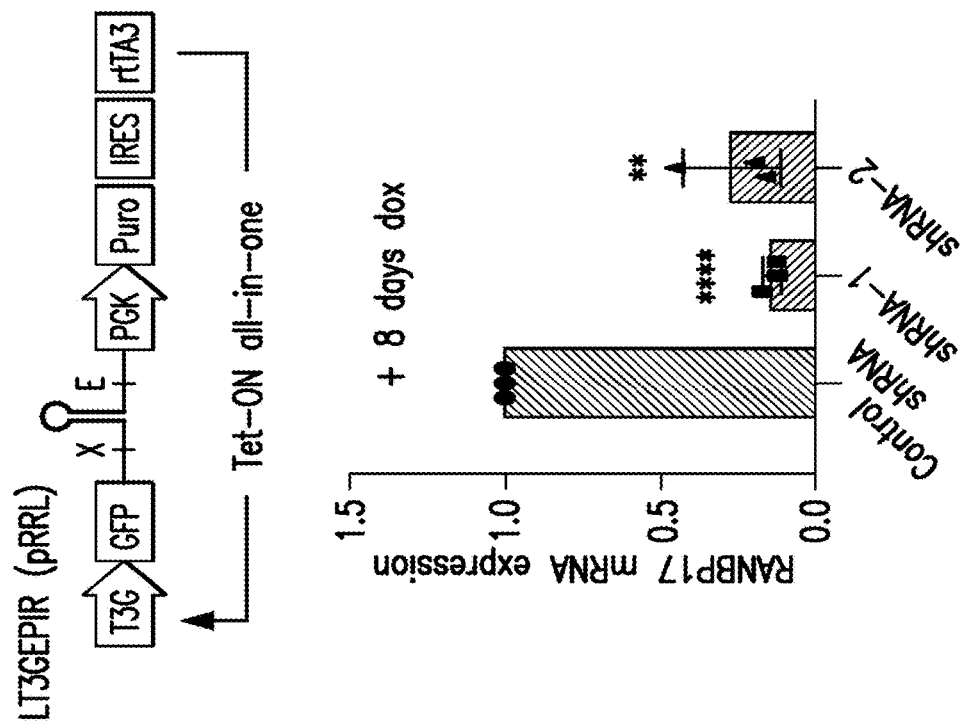

FIGS. 6A-6B. Manipulation of novel, candidate induced aging strategies in human iPSC-derived neural cell types. FIG. 6A: A broad range of human iPSC-derived neural cell types were transduced using lentiviral vectors tested for efficient inducible knockdown or overexpression. Example of using this vector for knockdown of RANBP17. FIG. 6B: Example of using CRISPR-a system to trigger activation of endogenous HERV-K in hPSCs and hPSC-derived neurons.

Figures 7A, 7B:
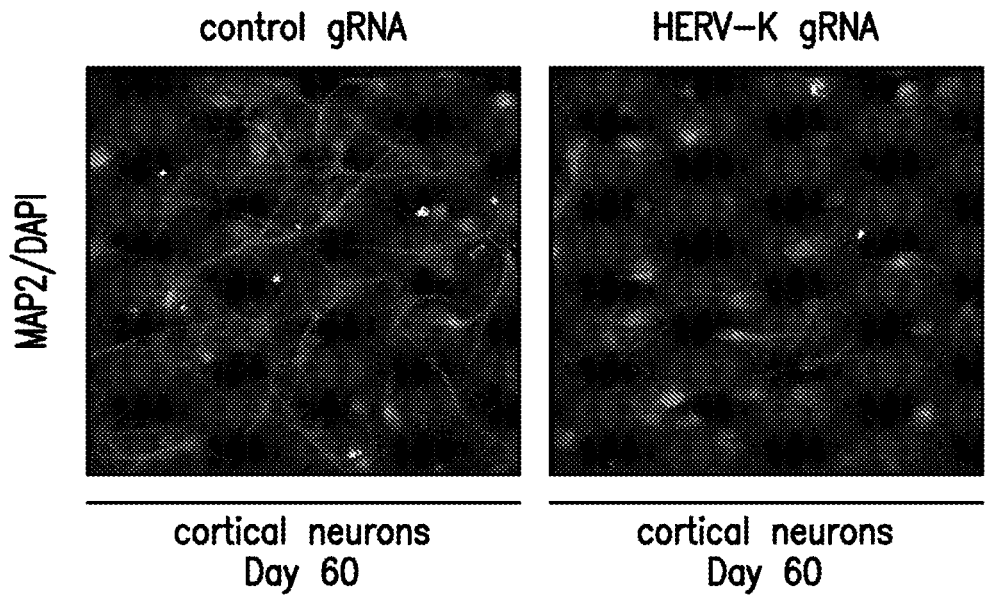
Figures 7C, 7D:
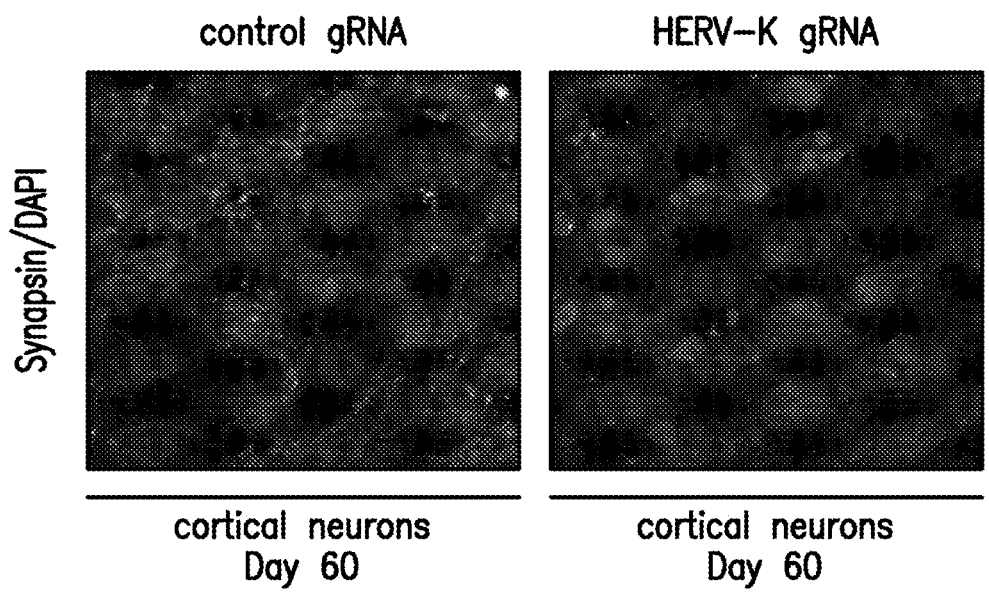

FIGS. 7A-7D. Activation of HERV-K expression in human PSC-derived cortical neurons triggered age-related changes. FIGS. 7A and 7B: Neurons treated with HERV-K gRNA showed reduced number and length of MAP2$^+$ neuronal processes compared to neurons treated with control gRNA, suggesting the induction of dendrite loss, a phenotype that is related to the induction of an age-like state in neurons. FIGS. 7C and 7D: Neurons treated with HERV-K gRNA showed reduced number of synaptic punctae (clusters of synaptic proteins expected to mark the site of neuronal synapses). Both reduction in the number of MAP2$^+$ processes and reduction in Synpasin$^+$ punctae occurred without an obvious loss of neuronal cell numbers indicating early signs of age-related degeneration rather than induction of frank toxicity.

5. DETAILED DESCRIPTION OF THE INVENTION

The present invention relates to the following methodology:

(i) Generation of a comprehensive "transcriptomic and epigenomic roadmap of human aging and rejuvenation" by profiling multiple layers of 2D and 3D genomic regulation, before and after reprogramming, across cell types;

(ii) Applying the identified transcriptomic and epigenomic principles of aging to design methods for cellular rejuvenation within a given cell type; and (iii) Applying therapeutically amenable strategies for directing rejuvenation of cells and tissues.

For clarity, and not by way of limitation, this detailed description is divided into subsections corresponding to (i)-(iii) above.

Herein, a subject may be a human or non-human, for example non-human primate, rodent, dog, cat, rabbit, or horse subject. Similarly, a cell or tissue may be a cell or tissue from any of the foregoing subjects.

For purposes of clarity of disclosure and not by way of limitation, the detailed description is divided into the following subsections:

5.1. Definitions
5.2. Transcriptional and epigenomic roadmap of cellular aging and rejuvenation across cell types;
5.3. Manipulating cell age independently of cell fate through transcriptional and epigenetic interventions; and
5.4. Therapeutic applications.

5.1 Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

"Transcriptional profile" or "transcriptomic profile" used herein refers to the levels of genome-wide gene expressions in cells or tissues at the transcription (RNA) level.

"Epigenetic profile" or "epigenome profile" used herein refers to epigenetic characteristics of genomic sequences in cells or tissues. Non-limiting examples of epigenetic characteristics include DNA methylation, DNA demethylation, histone methylation, histone demethylation, histone acetylation, histone deacetylation and combinations thereof.

"Transcriptomic aging signature" refers to a collection of transcriptomic changes associated with aging.

"Epigenomic aging signature" refers to a collection of epigenomic changes associated with aging.

5.2. Transcriptional and Epigenomic Roadmap of Cellular Aging and Rejuvenation Across Cell Types In recent years the aging field has turned its attention towards the relationship between aging and epigenetics, moved by growing evidence that across tissues and organisms, aging is accompanied by a variety of transcriptional and epigenetic alterations[8,9]. The concept that aging may be subject to transcriptional and epigenetic control is particularly attractive for the prospect of reversing its effects. A series of recent reports from the iPSC field provide strong support for this hypothesis, by showing that reprogramming is capable of reinstating youthful biological functionalities in cells from old individuals (FIG. 1)[2-6]. These findings imply that the transcriptional and epigenetic reprogramming at the basis of induced pluripotency may be a driving force of this "cellular rejuvenation". Understanding how known aspects of cellular aging can be erased by reprogramming could lead to the development of tools for reprogramming cell age independently of cell fate.

Provided herein are methods for determine how transcriptional and epigenomic features distinctive of aged cells are dynamically changed upon reprogramming and re-differentiation. In certain embodiments, a plurality, or cohort, of primary cells from young and old donors can be reprogrammed to iPSC and subsequently re-directed into their original cell type. Transcriptomic and epigenomic profiles of the primary cells are compared with the reprogrammed and re-differentiated iPSCs. This system allows for the comparison of cells from the same lineage and genetic background before and after reprogramming, thereby reducing the confounding effects of epigenetic heterogeneity across cell types and the genetic diversity of human samples.

In certain embodiments, the methods disclosed herein comprise determining tissue-specific transcriptomic and epigenomic aging signatures. In certain embodiments, the methods comprise comparing transcriptomic and epigenomic profiles in regionally defined primary human tissues (e.g., frontal cortex, substantia nigra regions of the brain) obtained from young and old donors, determining tissue-specific transcriptomic and epigenomic changes associated with aging. A transcriptomic or epigenomic aging signature is a collection of transcriptomic or epigenomic changes associated with aging. In certain embodiments, the methods further comprise identifying the transcriptomic and epigenomic changes that are reversed in re-differentiated iPSC-derived tissue-specific cells (e.g., iPSC-derived cortical or dopaminergic neurons).

In certain embodiments, said tissue-specific transcriptomic and epigenomic aging signatures from different tissues and said transcriptomic and epigenomic changes reversed upon iPSC reprogramming are combined to determine (1) universal transcriptomic and epigenomic aging markers that universally present in different tissues, and (2) universal transcriptomic and epigenomic mechanisms of rejuvenation which functionally determine and drive aging.

Transcriptomic and epigenomic aging signatures defined in primary cells through transcriptomic and epigenomic (e.g., DNA methylation) profiling can then be validated in independent primary or previously published datasets. The effects of reprogramming and re-differentiation on these signatures can then be analyzed.

A set of genomic markers that show age-dependent transcriptional and epigenetic alterations, identified by such methods, are set forth in Section 6 below. Age-dependent differences at these loci are lost in iPSC and in re-differentiated cells of both donor groups a transcriptionally and epigenetically "young" state is restored. These data suggest that through iPSC induction, old cells are stripped of a memory of age at the transcriptional and epigenetic level, while a young code is re-established.

Additional analysis can address whether inducing pluripotency can fully erase age-dependent epigenetic anomalies, which may extend to histone modifications and chromatin organization, leaving the genome truly rejuvenated, and also whether the age-resetting paradigm applies to different cell types and can act as a "universal" means of rejuvenation across tissues. Further, the identified epigenetic changes can be assessed for their impact on cellular processes to determine whether they play a causative role in the biology of aging.

The epigenetic changes may reside in a number of characteristics, including, for example but not by way of limitation, transcription and DNA methylation. Further, aging is known to affect multiple layers of epigenomic regulation, importantly histone modifications[8]. In certain embodiments of the invention, primary cells may be reprogrammed into iPSC and re-differentiated into the original cell type, as set forth above, and at each stage chromatin may be assessed to determine whether a young chromatin configuration is re-established, both at the level of the histone code and of tridimensional organization. Utilizing the experimental setting described above, based on reprogramming and re-differentiation within the same lineage, ChIP-Seq analysis of major histone marks can be performed in all three cell types (primary, iPSC and iPSC-derived) from cells of young and old individuals. Priority can be given to histone marks known to be affected by age across tissues and organisms. Epigenetic identity is a critical determinant of chromatin architecture and of the correct localization of genomic regions within the nuclear space. Hence, the widespread changes to the epigenetic landscape known to occur with aging suggest that three-dimensional chromatin architecture may also be significantly impaired, with severe consequences on nuclear and cellular functionality.

A major question for the use of iPSC in regenerative medicine is whether the rejuvenating effect of induced pluripotency is independent of the final re-differentiated lineage. The fetal-like nature of PSC-derived cells has been reported for a variety of cell types, yet it is unclear how faithfully this state recreates a truly rejuvenated cell. To address this issue, human iPSC may be differentiated into various lineages among the most relevant for human aging such as, but not limited to, neurons, cardiomyocytes, hepatocytes etc., taking advantage of the highly specialized protocols for directed differentiation developed in recent times by the stem cell field. Transcriptomic and epigenetic assays may then be used to determine the "epigenomic age" of the re-differentiated cells, using existing functional genomics databases across human tissues (e.g. EBI, GTex, GEO, etc.) as a reference for tissue-specific aging signatures. De novo profiling of selected tissues from young and old donors might be desirable if deposited data doesn't exhaustively cover a given tissue across a sufficiently wide age-span.

The foregoing methodology may be used to build a multilayered map across cell types, for example, human cell types, showing how aging affects the transcriptome and epigenome and which aging signatures are reversed by reprogramming. The ultimate goal is to uncover universal genomic principles that can impose and subsequently rescue an aged cellular state.

In another aspect, the genomic aging markers identified by the methods disclosed herein can be used for measuring cellular age. Particularly, the genomic aging markers universally present in different tissues can be used for measuring cellular age independent of tissue or cell types. In certain embodiments, the universal genomic aging marker is a NETO2 gene. Non-limiting examples of genomic aging markers include age-related genome sequences (e.g., coding genes and non-coding sequences) and epigenetic markers. In certain embodiments, the genome sequence is a coding gene. In certain embodiments, the coding gene is selected from the group consisting of NETO2, RANBP17, AQP1, and CADPS genes. In certain embodiments, the non-coding sequences are repetitive elements or transposons, or promoter sequences of repetitive elements or transposons. In certain embodiments, the non-coding sequence is selected from the group consisting of long interspersed nuclear elements (LINS), short interspersed nuclear elements (SINES), and endogenous retroviruses (ERVS). In certain embodiments, the target genome sequence is selected from the group consisting of HERV-K gene and L1 gene. In certain non-limiting embodiments, the epigenetic maker is selected from the group consisting of nucleic acid methylations, nucleic acid demethylation, histone methylations, histone demethylations, histone acetylation, and histone deacetylations. In certain non-limiting embodiments, the epigenetic marker is selected from the group consisting of H3K9me3, H3K27me3, and 5mC DNA methylation.

Provided herein are also methods for determining cellular age, including measuring the expression of genomic aging markers disclosed herein in a cell or tissue. In certain embodiments, the cell or tissue is obtained from a subject. In certain embodiments, the cellular age can be different from the subject's actual age, and a treatment can be administered to the subject in accordance with the cellular age measured by the method disclosed herein. In certain embodiments, the genomic aging marker is NETO2 gene.

5.3. Manipulating Cell Age Independently of Cell Fate Through Transcriptional and Epigenetic Interventions Using the information gleaned according to the preceding section, tools may be devised for reprogramming cell age, while preserving cell fate. The preceding section provides a set of transcriptional and epigenetic anomalies enriched in cells from old individuals that can be erased by reprogramming and maintained in a young state upon re-differentiation. The noted anomalies would reinforce the correlation between transcriptional and epigenetic reprogramming and a rejuvenated cellular state.

To address this, a set of functionally promising loci or regions, including cell type-specific and -independent sequences, can be manipulated or modified, and the impact of these modifications on cellular aging can be assessed. The identified age-related genome sequences can be genetically or epigenetically engineered to manipulate cell age or rejuvenate cells. This can be achieved, for example, by locus-directed transcriptional and epigenetic editing through CRISPR/Cas9 technology or other genetic engineering techniques, and/or genome-wide modulation of epigenetic marks using chemical compounds. In certain non-limiting embodiments, targeted epigenetic engineering is achieved by means of the CRISPR/Cas9 technology that fuses a catalytically inactive dCas9 with an epigenetic enzyme of choice, allowing for RNA-guided alteration of DNA- or histone modifications at selected loci[10]. When utilized for targeted epigenetic engineering, the system includes a "dead" Cas9 (dCas9) that is catalytically inactive, CRISPR RNA (crRNA, contains the RNA used by Cas9 to guide it to the correct section of host DNA along with a region that binds to tracrRNA (generally in a hairpin loop form) forming an active complex with Cas9), trans-activating crRNA (tracrRNA, binds to crRNA and forms an active complex with Cas9). CRISPR/Cas9 often employs a plasmid to transfect the target cells. The crRNA needs to be designed for each application as this is the sequence that Cas9 uses to identify and directly bind to the selected loci in a cell.

Non-limiting examples of epigenetic characteristics and modifications are DNA methylations, DNA demethylations, histone methylations, histone demethylations, histone acetylation, and histone deacetylations. Non-limiting examples of epigenetic enzymes are histone methyltransferases, histone demethylases, histone acetyltransferases, histone deacetylases, nucleic acid methyltransferases, and nucleic acid demethylases. Modulations of epigenetic characteristics in selected loci can down-regulate or up-regulate the expression of age-related target genome sequences disclosed herein.

None-limiting examples of target genome sequences can include coding genes and non-coding sequences. In certain embodiments, the target genome sequence is a coding gene. In certain embodiments, the coding gene is selected from the group consisting of NETO2, RANBP17, AQP1, and CADPS genes. In certain embodiments, the expression of NETO2 and/or RANBP17 genes are up-regulated by the epigenetic engineering methods disclosed herein to rejuvenate the cell. In certain embodiments, the promoter sequence of NETO2 and/or RANBP17 genes are demethylated by the epigenetic engineering methods disclosed herein to up-regulate the expression of NETO2 and/or RANBP17 genes to rejuvenate the cell. In certain embodiments, the expression of AQP1 and CADPS genes are down-regulated by the targeted epigenetic engineering methods disclosed herein to rejuvenate the cell.

In certain embodiments, the target genome sequence is a non-coding sequence. In certain embodiments, the non-coding sequences are repetitive elements or transposons, or promoter sequences of repetitive elements or transposons. In certain embodiments, the non-coding sequence is selected from the group consisting of long interspersed nuclear elements (LINS), short interspersed nuclear elements (SINES), and endogenous retroviruses (ERVS). In certain embodiments, the target genome sequence is selected from the group consisting of HERV-K, L1, promoter sequences of HERV-K, and promoter sequences of L1. In certain embodiments, the targeted epigenetic engineering methods disclosed herein rejuvenate the cell by down-regulating the expression of HERV-K.

Furthermore, the expression state of the aged-related target genome sequences (i.e., coding genes or non-coding sequences) can be modulated using genetic engineering systems and methods. In certain embodiments, the target genome sequences can be switched on or off via CRISPR-a and CRISPR-i, where dCas9 is combined to either a transcriptional activator or repressor[11]. In certain embodiments, expression of the target genome sequences can be down-regulated or knocked down using oligonucleotides that have complementary sequences to mRNA transcripts corresponding to the target genome sequences. Non-limiting examples of such oligonucleotides include small interference RNA (siRNA) and short hairpin RNA (shRNA). In certain embodiments, the expression of the target genome sequences can be overexpressed or upregulated by inserting a copy of the target genome sequence to the cell DNA. In certain embodiments, the target genome sequences are coding genes. In certain embodiments, the coding genes are selected from the group consisting of NETO2, RANBP17, AQP1, and CADPS genes. In certain embodiments, the expression of NETO2 and/or RANBP17 genes are activated or up-regulated by the genetic engineering methods disclosed herein to rejuvenate the cell. In certain embodiments, the expression of RANBP17 gene is downregulated by administrating an shRNA to the target cell to age the cell, and the shRNA have complementary sequence to the mRNA of RANBP17. In certain embodiments, the expression of AQP1 and CADPS genes are down-regulated or repressed by the genetic engineering methods disclosed herein to rejuvenate the cell. In certain embodiments, the target genome sequence is a non-coding sequence. In certain embodiments, the non-coding sequences are repetitive elements or transposons. In certain embodiments, the non-coding sequence is selected from the group consisting of long interspersed nuclear elements (LINS), short interspersed nuclear elements (SINES), and endogenous retroviruses (ERVS). In certain embodiments, the target genome sequence is selected from the group consisting of HERV-K and L1. In certain embodiments, the expression of HERV-K and/or L1 is upregulated using the genetic engineering methods disclosed herein to rejuvenate the cell. In certain embodiments, the expression of HERK is activated by administrating a CRISP-a/dCas9 epigenetic engineering system to the target cell to age the cell, and the dCas9 is fused with a transcription activator (e.g., VP64).

The epigenetic engineering system and genetic engineering system disclosed herein can be delivered into a target cell using a retroviral vector, e.g., gamma-retroviral vectors, and lentiviral vectors. Combinations of retroviral vector and an appropriate packaging line are suitable, where the capsid proteins will be functional for infecting human cells. Various amphotropic virus-producing cell lines are known, including, but not limited to, PA12 (Miller, et al. (1985) Mol. Cell. Biol. 5:431-437); PA317 (Miller, et al. (1986) Mol. Cell. Biol. 6:2895-2902); and CRIP (Danos, et al. (1988) Proc. Natl. Acad. Sci. USA 85:6460-6464). Non-amphotropic particles are suitable too, e.g., particles pseudotyped with VSVG, RD114 or GALV envelope and any other known in the art. Possible methods of transduction also include direct co-culture of the cells with producer cells, e.g., by the method of Bregni, et al. (1992) Blood 80:1418-1422, or culturing with viral supernatant alone or concentrated vector stocks with or without appropriate growth factors and polycations, e.g., by the method of Xu, et al. (1994) Exp. Hemat. 22:223-230; and Hughes, et al. (1992) J. Clin. Invest. 89:1817.

Other transducing viral vectors can be used to modify a target cell. In certain embodiments, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). Other viral vectors that can be used include, for example, adenoviral, lentiviral, and adena-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337: 1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; LeGal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for genetic engineering of a target cell. For example, a nucleic acid molecule can be introduced into the target cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of nucleic acid molecules into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically.

In certain non-limiting embodiments, global epigenetic changes are induced using epigenetically active drugs. A wide selection of these compounds, tailored to act on specific epigenetic enzymes, are available owing to their relevance for cancer therapy. In certain non-limiting embodiments, the epigenetic enzymes are selected from the group consisting of histone methyltransferases, histone demethylases, histone acetyltransferases, histone deacetylases, nucleic acid methyltransferases, and nucleic acid demethylases.

Key for evaluating the effect of these interventions on aging is the ability to measure cellular age. As described above in the preceding section, cells of aged individuals display a set of distinctive phenotypes, collectively termed 'cellular hallmarks of aging', most of which are readily quantifiable by imaging techniques[3]. In addition, genomic aging markers, e.g., epigenetic and transcriptional age-related markers disclosed herein (e.g., at Section 5.2), can also be used for measuring and evaluating cellular age. In addition, the phenotypic markers can be complemented with a set of genomic aging markers disclosed herein for accurately measuring cellular age.

A particularly attractive option is to conduct a large-scale drug- or CRISPR-screen for putative aging or rejuvenating factors combined with high-content analysis of known or newly identified aging hallmarks, which, analogously to iPSC-based disease modeling, would seek to rescue age-related, instead of disease-related, cellular dysfunctions.

5.4. Therapeutic Applications

Prolonged life expectancy is posing new challenges to health care, which is burdened by the rise in conditions that are a direct or indirect consequence of old age, such as neurodegeneration, cancer and cardiovascular diseases. Biomedical research can tackle this problem by either treating these pathologies as separate entities, or by addressing aging itself as their underlying cause for susceptibility. However, the urgency and appeal to get the handle on the biology of aging stands in stark contrast to the slow pace at which aging research has progressed. Somatic cell reprogramming, a 'game changer' for the study of human genetic disease, also represents a powerful tool for understanding and possibly treating diseases related to aging. The possibility of reversing cellular age through reprogramming opens unlimited possibilities for gaining mechanistic insight into this poorly understood process; insight that could be leveraged to control its inexorable course. Furthermore, understanding the depth of biological rejuvenation attained by reprogramming will be of extreme clinical relevance for the use of iPSC derived from old donors in cell replacement therapies. Finally, developing molecular strategies for directing cell age in vitro should pave the way for the long-term goal of therapeutic rejuvenation of whole tissues and organs, in vivo.

6. EXAMPLES

The presently disclosed subject matter will be better understood by reference to the following Example, which is provided as exemplary of the invention, and not by way of limitation.

Example 6.1

Identification of Transcriptional and Epigenetic Features of Cellular Aging

Transcriptional and epigenetic features of cellular aging that can be erased by reprogramming were investigated to identify functionally relevant mechanisms for the reacquisition of cellular youth. A cohort of primary fibroblasts (pFIB) from young and old donors, their matched iPSC and re-differentiated iPSC-derived fibroblasts (iPSC-FIB), were generated. Age signatures identified in primary fibroblasts were compared with those in matched iPSC-derived fibroblasts following rejuvenation. Complementary profiling strategies and perform validation studies across independent primary fibroblast samples were adopted to further expand the identification of age signatures. This experimental system offers the ability to compare cells of the same lineage and identical genetic background before and after reprogramming, thus eliminating the confounding effects of epigenetic variability between cell types and genetic diversity of human samples (FIG. 1A). The approach captured reliable molecular age signatures and identified candidate pathways for functional manipulations.

Whole-transcriptome analysis by Total RNA Seq and genome-wide DNA methylation profiling of both canonical methylation (5mC) and hydroxymethylation (5hmC) was performed. First, the bona fide fibroblast identity of the re-differentiated cells was validated using QC measures (FIGS. 2A-2D). Expression of the fibroblast and differentiation markers CD13 and HLA-ABC by FACS and Vimentin and Collagen by IHC (FIGS. 2A-2C) was comparable in primary and iPSC-derived fibroblasts. Examination of the expression patterns of the top differentially expressed genes indicated comparable profiles for primary and iPSC-derived fibroblast vs iPSCs (Pearson correlations: primary-Fib vs. iPSC-Fib 0.91, primary-Fib vs. iPSC −0.04, iPSC-Fib vs. iPSC −0.03, FIG. 2D). iPSC-FIB displayed levels of specific markers and gene expression profiles nearly identical to pFIB, confirming that the pre-reprogramming lineage is restored after re-differentiation (FIGS. 2A-2D).

Age-dependent transcriptional differences in pFIB and whether these differences were maintained or lost in the corresponding iPSC and iPSC-FIB were examined. More than 100 differentially expressed genes between young and old pFIB were detected (FIG. 3A). A downregulation of histone genes was observed, in agreement with the known age-dependent loss of core histones[19,20]. Expression of these genes in iPSC and iPSC-FIB was no longer biased for donor age and a near complete reset of the transcriptional age signature of old vs young pFIBs in iPSCs and iPSC-derived FIBS was observed (FIG. 3C), indicating a loss of the transcriptional aging signature after reprogramming. The RNA-Seq data was compared with a dataset of primary fibroblasts and brain tissue from young and old donors.[12] Nearly 20 genes were confirmed to have a same-directional change in expression with age in both fibroblast DATASETS. Among these, three genes (NETO2, RANBP17, AQP1) (FIG. 3B) were also differentially regulated with age in the brain, and may represent tissue-independent aging markers. The absolute levels of these tissue-independent aging genes, and that of a fourth gene that was among the top differentially expressed in fibroblasts (CADPS), changed upon reprogramming. Transcriptional levels of AQP1 and CADPS in iPSC-FIB of both donor ages were identical to those in young pFIB (FIG. 3D), while NETO2 and RANBP17 showed similar, yet higher expression in iPSC-FIB compared to young pFIB (~10-year old). The transcript levels of RANBP17 and NETO2 in fetal and newborn pFIB vs. pFIB from young adults (<20y) in the published dataset were compared, which confirmed a higher expression of these two genes in fetal and newborn samples (data not shown), and thus the discrepant expression between iPSC-FIB and young pFIB for these two genes reflects the fetal-like nature of iPSC-derivatives. Next, whether the return to a young-like transcription was mediated by a reset of epigenetic marks at these loci was determined. The levels of DNA methylation at the regulatory regions of these genes was extracted from a genome-wide 5mC analysis. For NETO2 and RANBP17, promoter CpG methylation closely correlated with the observed expression changes across the three cell types (FIG. 3E), while the transcriptional changes in AQP1 and CAPDS seemed to be controlled by methylation-independent mechanisms. DNA methylation state showed a similar pattern of rejuvenation both at global and site-specific levels (FIGS. 3E-3F). Additional passaging did not trigger age-related gene expression, suggesting that this signature is reflective of chronological rather than replicative aging. The reset of age-related molecular markers in iPSC-derived fibroblasts can be drivers of cellular aging.

NETO2 expression levels were further measured in primary fibroblasts obtained from young and old donors, confirming its role as an aging marker. In particular, NETO2 mRNA levels were higher in young primary fibroblasts than old primary fibroblasts (FIG. 5A, n=6; young donors, 7-13 years old; old donors, 83-87 years old). NETO2 protein levels in primary fibroblasts obtained from young and old showed similar differences; NETO protein levels were significantly higher in primary fibroblasts obtained from young donors than primary fibroblasts obtained from old donors (FIGS. 5B-5C).

Furthermore, a decrease of repressive epigenetic marks, such as H3K9me3, H3K27me3 and 5mC DNA methylation, is reported to occur with age across species and tissues,[3,9,]

15-18 and was confirmed in our primary fibroblasts (FIG. 4A). These epigenetic marks are associated with a nuclear compartment that provides for the correct regulation and structural integrity of the eukaryotic genome. Hence, an "erosion" of epigenetic silencing could lead to the transcriptional deregulation and surge in DNA damage characteristic of aged cells. Additionally, transcriptional data showed that a large portion of non-coding sequences, including repetitive elements and transposons, were aberrantly expressed in cells from old donors (FIG. 4B). The upregulation of distinct classes of repetitive endogenous, elements such as HERVs (human endogenous retroviruses) and LINE elements in old fibroblasts was a prominent result (FIG. 4B). Activation of these transposable elements and repetitive endogenous, elements represents a scenario that could link the loss of heterochromatin to DNA damage and transcriptional deregulation with age.

These results indicate that through iPSC induction, old cells are at least partially stripped of a genomic memory of age at the transcriptional and at the epigenetic level, while a young-like state is re-established.

Valid strategies were employed to trigger gain or loss of function of candidate genes in the cell types disclosed herein (FIGS. 6A-6B). Such strategies included traditional shRNA (FIG. 6A) and overexpression strategies as well as CRISPR-a based strategies triggering ectopic expression of HERV-K via a "dead" dCas9-VP64 mediated transcriptional activation (FIG. 6B). Depending on the expression mode of aging markers (gain or loss-of-function), overexpression or knockdown using lentiviral vectors or CRISPR-based strategies were employed. For example, loss-of-function for RANBP17 (FIG. 6A) and endogenous activation of HERV-K (FIG. 6B) were tested.

Epigenetic manipulations were based on the finding that loss of DNA methylation leads to transcriptional deregulation and expression of inappropriate transcripts such as endogenous retroviral elements including HERV and LINE (FIG. 4B). Hypomethylation-dependent activation of HERVs was previously shown to trigger an innate immune response in affected cells responding to the endogenous viral RNA[21,22]. We detected both RNA and protein expression of HERVK in aged cells, similar to data published for human pre-implantation embryo[23] and cancer cells upon 5aza treatment[24,25]. In addition to epigenetic strategies, a robust CRISPR-based platform was developed to selectively trigger HERV-K expression (FIG. 6B).

Activation of HERV-K expression in expression in human PSC-derived cortical neurons triggered age-related changes. Human PSC-derived cortical neurons were generated using the dual-SMAD inhibition method of neural induction. The hPSC-derived cortical neurons matured to day 60 of differentiation. A dCas9-VP64 gene was stably integrated to the differentiated hPSC line using method disclosed herein, to activate endogenous gene expression or expression of repetitive elements of interest (e.g., HREV-K), depending on the specific gRNA provided. To activate the expression of HERV-K, the neurons were treated with either control gRNA not targeting any known DNA region or the specific HERK-K gRNA of interest targeting the LTR-region of HERV-K. The expression of MAP2 and synapsin proteins in the transfected hPSC-derived cortical neurons were measured using immunofluorescence. Exemplary images were shown in FIGS. 7A-7D. Cortical neurons treated with HERV-K gRNA showed reduced number and length of MAP2$^+$ neuronal processes compared to cortical neurons treated with the control gRNA, suggesting the induction of dendrite loss, a phenotype that may be related to induction of an age-like state in neurons (FIGS. 7A-7B). Cortical neurons treated with the HERV-K gRNA also showed reduced number of synaptic punctae (clusters of synaptic proteins expected to mark the site of neuronal synapses) (FIG. 7C-7D). Both the reduction in the number of MAP2$^+$ processes and the reduction in Synpasin$^+$ punctae occurred without an obvious loss of neuronal cell numbers, indicating early signs of possibly age-related degeneration rather than induction of frank toxicity.

7. REFERENCES

1. Cornacchia, D. & Studer, L. Back and forth in time: Directing age in iPSC-derived lineages. *Brain Res* (2015).
2. Studer, L., Vera, E. & Cornacchia, D. Programming and Reprogramming Cellular Age in the Era of Induced Pluripotency. *Cell stem cell* 16, 591-600 (2015).
3. Miller, J. D., et al. Human iPSC-based modeling of late-onset disease via progerin-induced aging. *Cell stem cell* 13, 691-705 (2013).
4. Lapasset, L., et al. Rejuvenating senescent and centenarian human cells by reprogramming through the pluripotent state. *Genes & development* 25, 2248-2253 (2011).
5. Marion, R. M., et al. Telomeres acquire embryonic stem cell characteristics in induced pluripotent stem cells. *Cell stem cell* 4, 141-154 (2009).
6. Suhr, S. T., et al. Mitochondrial rejuvenation after induced pluripotency. *PloS one* 5, e14095 (2010).
7. Mahmoudi, S. & Brunet, A. Aging and reprogramming: a two-way street. *Current opinion in cell biology* 24, 744-756 (2012).
8. Benayoun, B. A., Pollina, E. A. & Brunet, A. Epigenetic regulation of ageing: linking environmental inputs to genomic stability. *Nature reviews. Molecular cell biology* 16, 593-610 (2015).
9. Fraga, M. F. & Esteller, M. Epigenetics and aging: the targets and the marks. *Trends in genetics: TIG* 23, 413-418 (2007).
10. Thakore, P. I., Black, J. B., Hilton, I. B. & Gersbach, C. A. Editing the epigenome: technologies for programmable transcription and epigenetic modulation. *Nat Methods* 13, 127-137 (2016).
11. Dominguez, A. A., Lim, W. A. & Qi, L. S. Beyond editing: repurposing CRISPR-Cas9 for precision genome regulation and interrogation. *Nature reviews. Molecular cell biology* 17, 5-15 (2016).
12. Mertens, J., et al. Directly Reprogrammed Human Neurons Retain Aging-Associated Transcriptomic Signatures and Reveal Age-Related Nucleocytoplasmic Defects. *Cell stem cell* 17, 705-718 (2015).
13. Glass, D., et al. Gene expression changes with age in skin, adipose tissue, blood and brain. *Genome Biol* 14, R75 (2013).
14. Bicakci, H., et al. Investigation of the effects of aging on the expression of aquaporin 1 and aquaporin 4 protein in heart tissue. *Anatol J Cardiol* (2016).
15. Lopez-Otin, C., Blasco, M. A., Partridge, L., Serrano, M. & Kroemer, G. The hallmarks of aging. *Cell* 153, 1194-1217 (2013).
16. Feser, J. & Tyler, J. Chromatin structure as a mediator of aging. *FEBS letters* 585, 2041-2048 (2011).
17. Horvath, S. DNA methylation age of human tissues and cell types. *Genome biology* 14, R115 (2013).
18. Johnson, A. A., et al. The role of DNA methylation in aging, rejuvenation, and age-related disease. *Rejuvenation research* 15, 483-494 (2012).

19. Ong, M. L. & Holbrook, J. D. Novel region discovery method for Infinium 450K DNA methylation data reveals changes associated with aging in muscle and neuronal pathways. *Aging cell* 13, 142-155 (2014).
20. Lister, R., et al. Global epigenomic reconfiguration during mammalian brain development. *Science* 341, 1237905 (2013).
21. Roulois, D., et al. DNA-Demethylating Agents Target Colorectal Cancer Cells by Inducing Viral Mimicry by Endogenous Transcripts. *Cell* 162, 961-973 (2015).
22. Chiappinelli, K. B., et al. Inhibiting DNA Methylation Causes an Interferon Response in Cancer via dsRNA Including Endogenous Retroviruses. *Cell* 162, 974-986 (2015).
23. Grow, E. J., et al. Intrinsic retroviral reactivation in human preimplantation embryos and pluripotent cells. *Nature* 522, 221-225 (2015).
24. Steinbeck, J. A., et al. Optogenetics enables functional analysis of human embryonic stem cell-derived grafts in a Parkinson's disease model. *Nature biotechnology* 33, 204-209 (2015).
25. Ganat, Y. M., et al. Identification of embryonic stem cell-derived midbrain dopaminergic neurons for engraftment. *J Clin Invest* 122, 2928-2939 (2012).

Various references are cited herein, the contents of which are hereby incorporated by reference in their entireties.

What is claimed is:

1. A method for reprograming cell age, comprising administrating to the cell an epigenetic engineering system, wherein the epigenetic engineering system alters an epigenetic characteristic at a NETO2 gene sequence of the cell.

2. The method of claim 1, wherein the epigenetic engineering system is a CRISPR/Cas9 system, which comprises a Cas9 molecule and a guided RNA (gRNA), wherein the Cas9 molecule is conjugated with an epigenetic enzyme, and the gRNA comprises a targeting domain that is complementary with a target sequence of the NETO2 gene sequence.

3. The method of claim 2, wherein the epigenetic enzyme is selected from the group consisting of histone methyltransferases, histone demethylases, histone acetyltransferases, histone deacetylases, nucleic acid methyltransferases, and nucleic acid demethylases.

4. The method of claim 2, wherein the Cas9 molecule is a d-Cas9 molecule.

5. The method of claim 2, wherein the epigenetic enzyme is a DNA demethylase, and
   (a) the expression of NETO2 gene sequence is upregulated; or
   (b) the NETO2 gene sequence comprises a promoter sequence of NETO2 gene, wherein the expression of NETO2 gene is upregulated.

6. The method of claim 1, wherein the epigenetic characteristic is selected from the group consisting of a DNA methylation, a DNA demethylation, a histone methylation, a histone demethylation, a histone acetylation, a histone deacetylation and combinations thereof.

7. The method of claim 1, wherein the NETO2 gene sequence comprises a sequence selected from the group consisting of coding sequences, regulatory sequences, and non-coding sequences.

8. A method for reprogramming cell age, comprising administrating to the cell a genetic engineering system, wherein the genetic engineering system alters the expression of a NETO2 gene sequence of the cell; wherein the genetic engineering system is a CRISPR/Cas9 system, which comprises a Cas9 molecule and a guided RNA (gRNA), wherein the Cas9 molecule is conjugated to a transcription modulator, and the gRNA comprises a targeting domain that is complementary with a target sequence of the NETO2 gene sequence.

9. The method of claim 8, wherein the genetic engineering system upregulates the expression of NETO2 gene.

* * * * *